United States Patent
Diker et al.

(10) Patent No.: US 11,718,586 B2
(45) Date of Patent: Aug. 8, 2023

(54) METHOD FOR PREPARING DEXMEDETOMIDINE

(71) Applicant: NORCHIM, Saint-Leu d'Esserent (FR)

(72) Inventors: Khalid Diker, Saint-Maximin (FR); Gilles Gorins, Le Perreux sur Marne (FR); Aurélie Ozanne-Beaudenon, Saint Leu d'Esserent (FR); Corinne Goldstein, Fes Lilas (FR)

(73) Assignee: NORCHIM, Saint-Leu d'Esserent (FR)

( * ) Notice: Subject to any disclaimer, the term of this patent is extended or adjusted under 35 U.S.C. 154(b) by 0 days.

(21) Appl. No.: 17/775,119

(22) PCT Filed: Nov. 9, 2020

(86) PCT No.: PCT/EP2020/081530
§ 371 (c)(1),
(2) Date: May 6, 2022

(87) PCT Pub. No.: WO2021/089878
PCT Pub. Date: May 14, 2021

(65) Prior Publication Data
US 2022/0363647 A1    Nov. 17, 2022

(30) Foreign Application Priority Data
Nov. 8, 2019 (EP) .................................... 19306457

(51) Int. Cl.
*C07D 233/58* (2006.01)
(52) U.S. Cl.
CPC .................. *C07D 233/58* (2013.01)
(58) Field of Classification Search
CPC .................................................. C07D 233/58
See application file for complete search history.

(56) References Cited

FOREIGN PATENT DOCUMENTS

| CN | 101921234 B | 5/2012 |
| CN | 106083724 A | 11/2016 |

(Continued)

OTHER PUBLICATIONS

Cordi et al., "Efficient Synthesis of (S)-4(5)-[1-(2,3-Dimethylphenyl) Ethyl]Imidazole Tartrate, the Potent α₂ Adrenoceptor Agonist Dexmedetomidine", Synthetic Communications, 1996, vol. 26, No. 8, pp. 1585-1593.

(Continued)

*Primary Examiner* — Rebecca L Anderson
(74) *Attorney, Agent, or Firm* — Birch, Stewart, Kolasch & Birch, LLP

(57) ABSTRACT

The present invention relates to a method for preparing dexmedetomidine having the following formula (I): or a pharmaceutically acceptable salt and/or solvate thereof, comprising the following successive steps: a) asymmetric hydrogenation of a methylene derivative of the following formula (II): in order to obtain dexmedetomidine, and b) optionally salifying and/or solvating dexmedetomidine in order to obtain a pharmaceutically acceptable salt and/or solvate of dexmedetomidine, wherein the methylene derivative of formula (II) is prepared from a halide of the following formula (V), in which Hal₂ represents a halogen atom such as Br, and a cyanoimidazole of the following formula (VI). The present invention relates also to methods for preparing synthesis intermediates of dexmedetomidine from the halide of formula (V) and the cyanoimidazole of formula (VI), these synthesis intermediates being the methylene derivative of formula (II), an alcohol of the following formula (III), and a ketone of the following formula (IV).

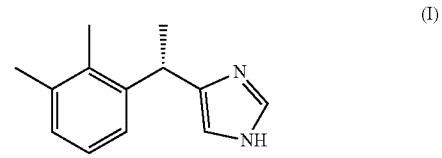

(I)

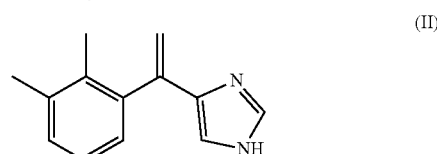

(II)

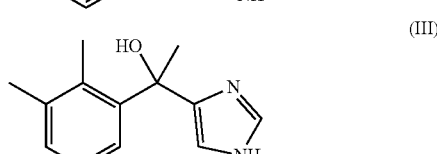

(III)

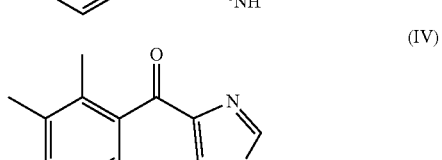

(IV)

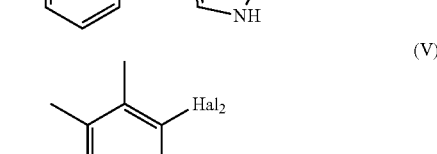

(V)

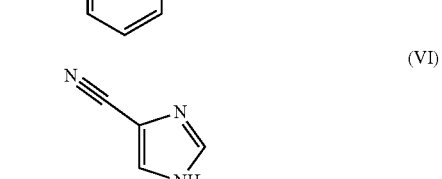

(VI)

16 Claims, No Drawings

(56) References Cited

FOREIGN PATENT DOCUMENTS

| | | |
|---|---|---|
| CN | 108147999 A | 6/2018 |
| CN | 109912508 A | 6/2019 |
| JP | 2018-39757 A | 3/2018 |

OTHER PUBLICATIONS

International Preliminary Report on Patentability for PCT/EP2020/081530 (PCT/IPEA/409) dated Nov. 4, 2021.
International Search Report for PCT/EP2020/081530 dated Feb. 5, 2021.
Written Opinion of the International Searching Authority for PCT/EP2020/081530 (PCT/ISA/237) dated Feb. 5, 2021.

METHOD FOR PREPARING DEXMEDETOMIDINE

TECHNICAL FIELD

The present invention relates to a method for preparing dexmedetomidine or a pharmaceutically acceptable salt and/or solvate thereof, and more particularly its hydrochloride salt, via the asymmetric hydrogenation of a methylene derivative. The present invention relates also to methods for preparing various synthetic intermediates of dexmedetomidine.

BACKGROUND

Dexmedetomidine, also called D-medetomidine or 4-[(1S)-1-(2,3-Dimethylphenyl)ethyl]-1H-imidazole, has the following formula (I):

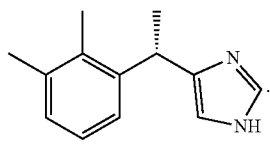

(I)

It is the dextrorotatory enantiomer of medetomidine. The levorotatory enantiomer of medetomidine is called L-medetomidine or levomedetomidine and has the following formula (I'):

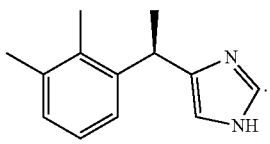

(I')

Dexmedetomidine is an α2-agonist sedative drug used in human and veterinary anesthesia. No pharmacological property has been reported for levomedetomidine. Thus, dexmedetomidine is about twice as powerful as medetomidine, the racemic mixture. It is thus preferable to administer dexmedetomidine instead of medetomidine.

Most of the methods reported in the literature to prepare dexmedetomidine involve the preparation of medetomidine, i.e. the racemic mixture, and the separation of the enantiomers via the formation of a diastereoisomer salt. However, in order to obtain dexmedetomidine with a satisfying enantiomeric excess allowing its use as a drug in animal, including man, multiple recrystallisation steps are necessary.

JP2018-39757 discloses a method involving an asymmetric reduction of a methylene derivative. However, this methylene derivative has to be in a protected form (protection of the NH function of the imidazole unit) to perform the reduction step so that additional steps of protection and deprotection are necessary.

Moreover, the methods for preparing dexmedetomidine can comprise the coupling between a molecule comprising a 2,3-dimethyl-phenyl unit and a molecule comprising an imidazole unit so as to form the skeleton of dexmedetomidine. In such a coupling, it is necessary to protect the NH function of the imidazole unit (e.g. CN108147999, CN109912508 or CN106083724) in order to avoid secondary reactions and the formation of by-products so that the method also involves additional steps of protection and deprotection of this unit.

There is thus a need for developing new methods for synthesizing dexmedetomidine in an efficient manner with a high selectivity and a high enantiomeric excess (e.e.) and a reduced number of steps.

SUMMARY OF THE INVENTION

The inventors have developed a method for preparing dexmedetomidine, or a pharmaceutically acceptable salt and/or solvate thereof, that allows responding to such a need.

This method uses an asymmetric hydrogenation of an unprotected methylene derivative, allowing the preparation of dexmedetomidine with a reduced number of steps and with a high selectivity. The asymmetric hydrogenation allows obtaining dexmedetomidine with a high enantiomeric excess, notably of at least 70%, which can be further increased by an enantiomeric enrichment step which does necessitate numerous recrystallisation steps.

The method also involves the coupling between 2,3-dimethylhalobenzene (compound of formula (V) below) and 4-cyanoimidazole (compound of formula (VI) below) in which the NH function of 4-cyanoimidazole is first deprotonated to form a magnesium halide derivative in situ, so as to avoid any secondary reaction on the NH function of this unit. The function is then reprotonated at the end of the coupling. In such a way, it is not necessary to perform specific protecting and deprotecting steps of this function.

According to a first aspect, the present invention relates to a method for preparing dexmedetomidine having the following formula (I):

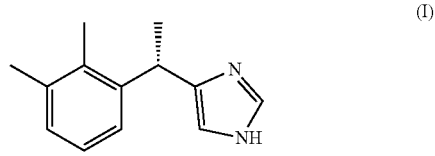

(I)

or a pharmaceutically acceptable salt and/or solvate thereof, comprising the following successive steps:

a) asymmetric hydrogenation of a methylene derivative of the following formula (II):

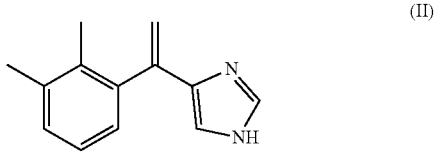

(II)

in order to obtain dexmedetomidine, and b) optionally salifying and/or solvating dexmedetomidine in order to obtain a pharmaceutically acceptable salt and/or solvate of dexmedetomidine.

Step a), more particularly performed in the presence of dihydrogen and a chiral catalyst of formula (A) as defined below, allows the enantioselective formation of the desired stereocenter, by asymmetric hydrogenation of the corresponding methylene group in the presence of a chiral ligand with a high enantiomeric excess. This enantiomeric excess can be further improved by the formation and separation of diastereoisomer salts along with a crystallisation step.

Step b) allows the formation of a pharmaceutically acceptable salt and/or solvate of dexmedetomidine, if required, such as the hydrochloride salt of dexmedetomidine.

The methylene intermediate of formula (II), at the core of this synthesis method, is more particularly prepared from a halide of the following formula (V):

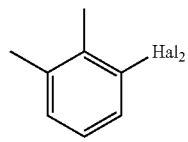
(V)

in which Hal$_2$ represents a halogen atom such as Br, and a nitrile of the following formula (VI) also called below cyanoimidazole of formula (VI):

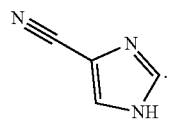
(VI)

Notably, the methylene intermediate of formula (II) is obtainable by acid-promoted dehydration of the corresponding tertiary alcohol, which can be synthesized in two steps from the corresponding aryl halide of formula (V) (e.g. aryl bromide) and cyanoimidazole of formula (VI) via the formation of the corresponding ketone. Thus, the methylene intermediate of formula (II) is advantageously prepared according to the following steps:

i) coupling the halide of formula (V) with the cyanoimidazole of formula (VI) in order to obtain a ketone of the following formula (IV):

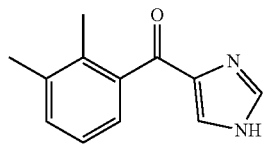
(IV)

according to the following steps:
  converting the halide of formula (V) into a Grignard reagent, notably in the presence of magnesium;
  deprotonating the cyanoimidazole of formula (VI) with AlkMgHal$_3$ in which Alk represents a (C$_1$-C$_6$)alkyl, notably a (C$_1$-C$_4$)alkyl such as iPr, and Hal$_3$ represents a halogen atom such as Cl or Br, notably Cl, to form the corresponding magnesium halide derivative (i.e. the hydrogen of the NH function of the imidazole moiety is replaced by the group MgHal$_3$),
  reacting the Grignard reagent with the magnesium halide derivative and then hydrolysing, notably by treatment with an acid such as sulfuric acid, notably in an aqueous solution, the reaction product thus obtained in order to form the ketone of formula (IV);

ii) methylating the ketone of formula (IV) in order to obtain an alcohol of the following formula (III):

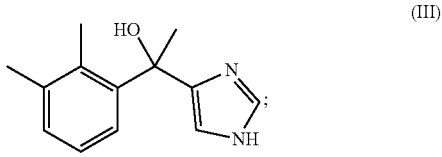 [SMILES: Cc1cccc(C(C)(O)c2c[nH]cn2)c1C]
(III)

and
iii) dehydrating the alcohol of formula (III) in order to obtain the methylene derivative of formula (II).

According to a second aspect, the present invention relates also to a method for preparing the ketone of formula (IV) (as synthesis intermediate of dexmedetomidine), or a pharmaceutically acceptable salt and/or solvate thereof, by coupling the halide of formula (V) with the cyanoimidazole of formula (VI) according to the following steps:
  converting the halide of formula (V) into a Grignard reagent, notably in the presence of magnesium;
  deprotonating the cyanoimidazole of formula (VI) with AlkMgHal$_3$ in which Alk represents a (C$_1$-C$_6$)alkyl, notably a (C$_1$-C$_4$)alkyl such as iPr, and Hal$_3$ represents a halogen atom such as Cl or Br, notably Cl, to form the corresponding magnesium halide derivative,
  reacting the Grignard reagent with the magnesium halide derivative and then hydrolysing, notably by treatment with an acid such as sulfuric acid, notably in an aqueous solution, the reaction product thus obtained in order to form the ketone of formula (IV).

According to a third aspect, the present invention relates also to a method for preparing the alcohol of formula (III) (as synthesis intermediate of dexmedetomidine), or a pharmaceutically acceptable salt and/or solvate thereof, comprising the following steps:
  preparing a ketone of formula (IV) by the method according to the second aspect, and
  methylating the ketone of formula (IV) in order to obtain the alcohol of formula (III).

According to a fourth aspect, the present invention relates to a method for preparing the methylene derivative of formula (II) (as synthesis intermediate of dexmedetomidine), or a pharmaceutically acceptable salt and/or solvate thereof, comprising the following steps:
  preparing an alcohol of formula (III) by the method according to the third aspect, and
  dehydrating the alcohol of formula (III) in order to obtain the methylene derivative of formula (II).

In the above-mentioned methods, the pharmaceutically acceptable salts and/or solvates of the compounds can be obtained by salifying and/or solvating said compounds, notably in the last step of the method.

Definitions

For the purpose of the invention, the term "pharmaceutically acceptable" is intended to mean what is useful to the preparation of a pharmaceutical composition, and what is generally safe and non-toxic, for a pharmaceutical use in an animal, including man.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as formic, acetic, benzenesulfonic, fumaric, glucoheptonic, gluconic, glutamic, glycolic, hydroxynaphthoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like, and (2) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The term "stereoisomers" used in this invention refers to optical isomers. Optical isomers result from the different position in space of substituents or lone pair of electrons on an atom (a carbon atom here) comprising four different substituents (including potentially a lone pair of electrons). This atom thus represents a chiral or asymmetric center. Optical isomers which are not mirror images of one another are thus designated as "diastereoisomers" and optical isomers which are non-superimposable mirror images are designated as "enantiomers".

An equimolar mixture of two enantiomers is designated as racemate or racemic mixture.

A "chiral" molecule (e.g. ligand, catalyst, acid) is a molecule which comprises a chiral center and which is non-superimposable to its mirror image. It is in the form of one enantiomer.

A "non-chiral" molecule is a molecule which is superimposable to its mirror image.

The "enantiomeric excess" (e.e. or % e.e.) reflects the degree to which a sample contains one enantiomer in greater amounts than the other. The enantiomeric excess can be calculated as follows: e.e.=IR−SI/(R+S)×100 where R is the amount in moles of one of the enantiomer and S is the amount in moles of the other enantiomer. Thus, a racemic mixture has an e.e. of 0%, while a single completely pure enantiomer has an e.e. of 100%. A sample containing 85% of one enantiomer and 15% of the other has an e.e. of 70%.

The term "asymmetric hydrogenation" used in this invention refers to a chemical reaction that adds two atoms of hydrogen on an unsaturated unit of a molecule, namely a C=C unit in the present invention, said addition being made preferentially on one side of said unsaturated unit so as to form preferentially one of the two enantiomers of the molecule bearing the unsaturated unit. Advantageously, the asymmetric hydrogenation allows obtaining the desired enantiomer with an enantiomeric excess of at least 70%.

The term "halogen", as used in the present invention, refers to a fluorine, bromine, chlorine or iodine atom.

The term "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like. It can be a methyl (Me), ethyl (Et), isopropyl (iPr) or t-butyl (tBu) group, such as isopropyl or t-butyl. Advantageously, it is a methyl (Me), ethyl (Et) or t-butyl (tBu) group, such as t-butyl.

The term "$(C_1-C_6)$haloalkyl", as used in the present invention, refers to a $(C_1-C_6)$alkyl group as defined above in which part or all of the hydrogen atoms is replaced with a halogen atom as defined above, such as a fluorine. This means that the $(C_1-C_6)$alkyl group is substituted by at least one halogen atom. It can be for example a trifluoromethyl ($CF_3$) group.

The term "$(C_1-C_6)$alkoxy", as used in the present invention, refers to a $(C_1-C_6)$alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like. Advantageously, it is a methoxy (OMe) group.

The term "$(C_1-C_6)$alkylamino", as used in the present invention, refers to a $(C_1-C_6)$alkyl group as defined above bound to the molecule via a NH group. It can be for example a methylamino, ethylamino, n-propyl-amino, iso-propylamino, n-butylamino, iso-butyl-amino, sec-butylamino, t-butylamino, n-pentylamino, n-hexyalmino, and the like.

The term "di(($C_1-C_6$)alkyl)amino", as used in the present invention, refers to a NRR' group where R and R', identical or different, represent a $(C_1-C_6)$alkyl group as defined above. It can be for example a dimethylamino, diethylamino, methyl-ethylamino, di-n-propyl-amino, di-iso-propylamino, di-n-butylamino, di-iso-butyl-amino, di-sec-butylamino, di-t-butylamino, di-n-pentylamino, di-n-hexylamino, and the like.

The term "$(C_3-C_{10})$cycloalkyl", as used in the present invention, refers to a hydrocarbon ring having 3 to 10, notably 3 to 7, such as 5 or 6, carbon atoms including, but not limited to, cyclopropyl, cyclopentyl, cyclohexyl and the like. Preferably, it is a cyclohexyl (Cy) group.

The term "aryl", as used in the present invention, refers to an aromatic hydrocarbon group comprising preferably 6 to 10 carbon atoms and comprising one or more fused rings, such as, for example, a phenyl (Ph) or naphthyl (Naph) group. Advantageously, it will be a phenyl group.

The term "heteroaryl", as used in the present invention, refers to an aromatic group comprising one or several, notably one or two, fused hydrocarbon cycles in which one or several, notably one to four, advantageously one or two, carbon atoms each have been replaced with a heteroatom selected from a sulfur atom, an oxygen atom and a nitrogen atom, preferably selected from an oxygen atom and a nitrogen atom. It can be in particular a 5-membered or 6-membered monocyclic heteroaryl group comprising 1 or 2 heteroatoms selected from N, O and S, and preferably from N and O. It can be a furyl, thienyl, pyrrolyl, pyridyl, oxazolyl, isoxazolyl, thiazolyl, isothiazolyl, imidazolyl, pyrazolyl, oxadiazolyl, thiadiazolyl, triazolyl, tetrazolyl, pyridazinyl, pyrimidinyl, pyrazinyl, triazinyl, quinolyl, isoquinolyl, quinoxalyl or indyl. Advantageously, it is a furyl.

The term "about" means in the context of the present invention that the concerned value may be lower or higher by 10%, especially by 5%, in particular by 1%, than the value indicated.

DETAILED DESCRIPTION

Preparation of Dexmedetomidine:

The method according to the present invention for preparing dexmedetomidine or a pharmaceutically acceptable salt and/or solvate thereof comprises the following successive steps:

a) asymmetric hydrogenation of a methylene derivative of the following formula (II):

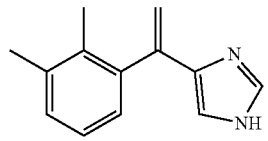
(II)

in order to obtain dexmedetomidine, and b) optionally salifying and/or solvating dexmedetomidine in order to obtain a pharmaceutically acceptable salt and/or solvate of dexmedetomidine.

According to a preferred embodiment, the method according to the present invention allows preparing a pharmaceutically acceptable salt of dexmedetomidine, and more particularly dexmedetomidine hydrochloride.

Dexmedetomidine or a pharmaceutically acceptable salt and/or solvate thereof, such as dexmedetomidine hydrochloride, is advantageously obtained, at the end of the method according to the invention, with an enantiomeric excess of from 99.0% to 100%, notably from 99.5% to 100%, preferably from 99.7% to 100%, more preferably from 99.9% to 100%, and even more preferably from 99.95% to 100%.

Step a):

The asymmetric hydrogenation of step a) can be performed in the presence of dihydrogen and a chiral catalyst such as a chiral catalyst of the following formula (A), notably of the following formula (A'):

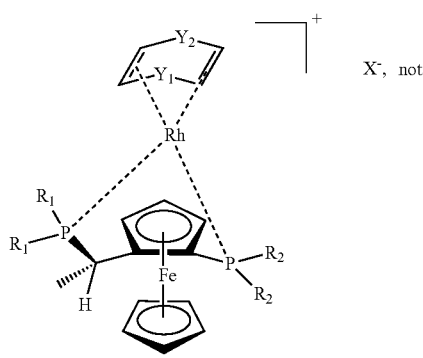
(A)
X⁻, notably

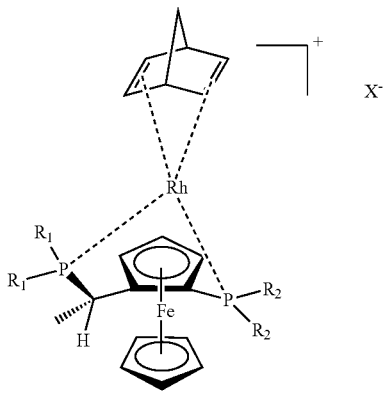
(A')

in which:

X⁻ is a counter-anion bearing one negative charge such as $BF_4^-$;

$Y_1$ and $Y_2$ form together a chain CH—$CH_2$—CH or each Y1 and $Y_2$ represent a group $CH_2CH_2$; and $R_1$ and $R_2$ independently of each other represent a ($C_1$-$C_6$)alkyl (e.g. Me, Et or tBu), a ($C_3$-$C_{10}$)cycloalkyl (e.g. Cy), a heteroaryl (e.g. furyl) or an aryl (e.g. Ph or Naph) optionally substituted by one or several, notably one, two or three, groups selected from ($C_1$-$C_6$)alkyl (e.g. Me), ($C_1$-$C_6$)haloalkyl (e.g. $CF_3$), ($C_1$-$C_6$)alkoxy (e.g. OMe), ($C_1$-$C_6$)alkylamino and di(($C_1$-$C_6$)alkyl)amino.

Advantageously, $R_1$ and $R_2$ independently of each other represent a ($C_1$-$C_6$)alkyl (e.g. Me, Et or tBu), a ($C_3$-$C_{10}$)cycloalkyl (e.g. Cy) or an aryl (e.g. Ph or Naph) optionally substituted by one or several, notably one, two or three, groups selected from ($C_1$-$C_6$)alkyl (e.g. Me), ($C_1$-$C_6$)haloalkyl (e.g. $CF_3$) and ($C_1$-$C_6$)alkoxy (e.g. OMe).

In particular, $R_1$ and $R_2$ independently of each other can be selected from methyl, ethyl, t-butyl, cyclohexyl, furyl, phenyl, naphthyl, 2-methyl-phenyl, 4-trifluoromethyl-phenyl, 4-methoxy-phenyl, 4-t-butyl-phenyl, 3,5-dimethyl-phenyl, 3,5-bis-trifluoromethyl-phenyl and 3,5-di-t-butyl-4-methoxy-phenyl. Preferably, $R_1$ is a t-butyl and $R_2$ is a phenyl.

When $Y_1$ and $Y_2$ form together a chain CH—$CH_2$—CH, then

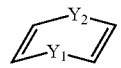

represents a norbornadiene unit.

When each Y1 and $Y_2$ represent a group $CH_2CH_2$, then

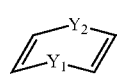

represents a 1,5-cyclooctadiene (COD) unit.

Preferably, $Y_1$ and $Y_2$ form together a chain CH—$CH_2$—CH.

X is a counter-anion bearing one negative charge which can be $BF_4^-$ or $PF_6^-$, preferably $BF_4^-$.

According to a preferred embodiment, the chiral catalyst has the following formula (A'-1):

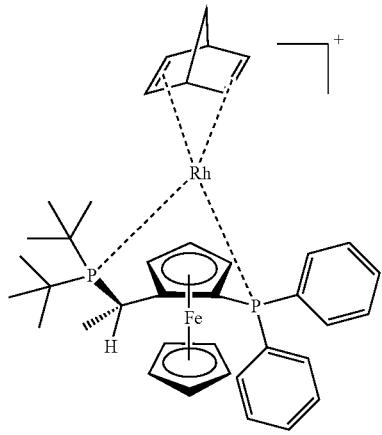
(A'-1)

The chiral catalyst of formula (A) can be prepared from:
a non-chiral rhodium-based catalyst of following formula (B), notably of following formula (B-1), such as the bis(norbornadiene) rhodium tetrafluoroborate of formula (B'-1):

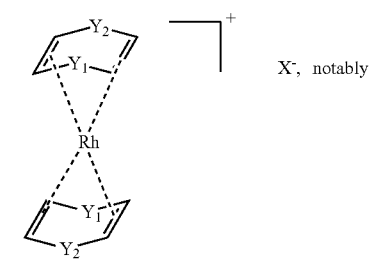
(B)

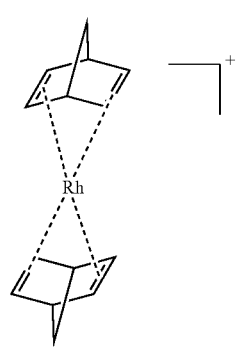
(B-1)

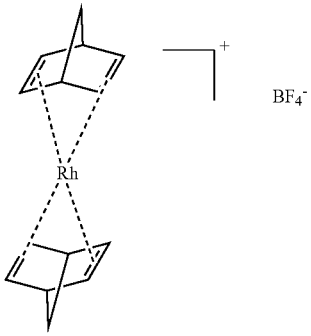
(B'-1)

with $Y_1$, $Y_2$ and X as defined above, and
a chiral ligand of the following formula (C), i.e. a chiral ligand of the Josiphos group, such as (S)-(+)-1-[(R)-2-(diphenylphosphino)ferrocenyl]ethylditertbutylphosphine of formula (C-1):

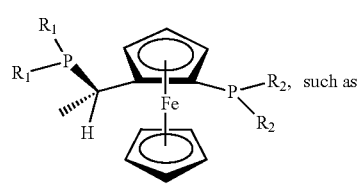
(C)

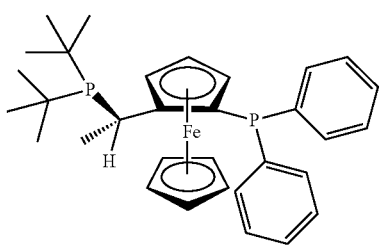
(C-1)

in which $R_1$ and $R_2$ are as defined above.

Compounds of formulas (B) and (C) will advantageously be used in step a) in the following amounts:
  amount of non-chiral catalyst of formula (B): from 0.001 to 0.1 mol, notably from 0.002 to 0.05 mol, preferably from 0.005 to 0.02 mol, such as about 0.01 mol per mole of methylene derivative of formula (II) used in step a);
  amount of chiral ligand of formula (C): from 0.001 to 0.1 mol, notably from 0.002 to 0.05 mol, preferably from 0.005 to 0.02 mol, such as about 0.01 mol per mole of methylene derivative of formula (II) used in step a).

Advantageously, the non-chiral catalyst of formula (B) and the chiral ligand of formula (C) are used in stoichiometric amounts, i.e. they are used in the same amounts in moles.

Advantageously, compounds of formulas (B) and (C) are mixed together in order to form the chiral catalyst of formula (A) before being added to the reaction medium containing the methylene derivative of formula (II). Preferably, the solvent used to mix together compounds of formulas (B) and (C) is the same as the one of the reaction medium, such as methanol.

Thus, the chiral catalyst of formula (A) is advantageously used in an amount of from 0.001 to 0.1 mol, notably from 0.002 to 0.05 mol, preferably from 0.005 to 0.02 mol, such as about 0.01 mol per mole of methylene derivative of formula (II) used in step a).

Step a) can be carried out at a temperature of from 40 to 60° C., notably at about 50° C. Step a) can be carried out under 5 to 15 bars, notably 8 to 12 bars, such as about 10 bars, of dihydrogen. Step a) can be carried out in a solvent such as methanol. In this case, methanol can be used in an amount of from 7.5 L to 120 L, notably from 10 L to 80 L, such as from 30 L to 50 L, preferably at about 45 L, for 1 kg of compound of formula (II).

Step a) allows the formation of dexmedetomidine with a high selectivity compared to levomedetomidine. Thus, dexmedetomidine is obtained in step a) with an enantiomeric excess of at least 70%, notably from 70% to 90%, preferably from 74% to 80%.

This enantiomeric excess can be increased by performing a step a') of enantiomeric enrichment after step a), and preferably before step b). Thus, dexmedetomidine is advantageously obtained in step a') with an enantiomeric excess of from 95.0% to 100%, notably from 99.0% to 100%, such as from 99.4% to 100%, preferably from 99.5% to 100% and more preferably from 99.8% to 100%.

The step a') of enantiomeric enrichment can be performed by:

a'1) reacting the product of step a) with a chiral acid such as L-tartaric acid or dibenzoyl-L-tartaric acid in order to form diastereoisomer salts including a salt formed with dexmedetomidine (i.e. the salt formed between the chiral acid and dexmedetomidine, the other salt being the salt formed between the chiral acid and levomedetomidine);

a'2) separating and recovering the salt formed with dexmedetomidine;

a'3) optionally recrystallizing the salt formed with dexmedetomidine;

a'4) converting the salt formed with dexmedetomidine into dexmedetomidine, notably in the presence of a base such as sodium hydroxide;

a'5) optionally recrystallizing dexmedetomidine.

Advantageously, steps a'1), a'2) and a'3) are performed in a solvent selected from acetone, methanol, ethanol, isopropanol, acetonitrile, tetrahydrofuran, ethyl acetate, water such as deionized water, and mixtures thereof. Preferably, step a'1) is performed in a mixture of acetone and water such as a mixture of acetone and deionized water, and steps a'2) and a'3) are performed in a mixture of ethanol and water such as a mixture of ethanol and deionized water. Step a1') can be performed at a temperature of from 40° C. to 60° C., such as from 45° C. to 50° C. Steps a'4) and a'5) can be performed in a solvent such as water, in particular deionized water.

Step a'2) more particularly involves the crystallization of the salt formed with dexmedetomidine and its separation from the reaction medium by filtration so as to be recovered. The final product of step a'4) is also advantageously in a crystallized form which can be recovered by filtration. For steps a'3) and a'5) of recrystallisation, the crystallized form is notably recovered by filtration.

Preparation of Methylene Derivative of Formula (II):

The methylene derivative of formula (II) can be prepared by dehydration of an alcohol of the following formula (III):

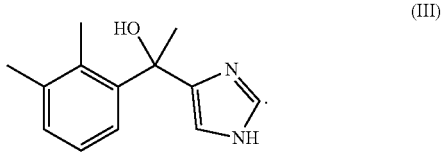 [SMILES: Cc1cccc(C(C)(O)c2c[nH]cn2)c1C]

This dehydration reaction can be performed in the presence of an acid such as para-toluenesulfonic acid (PTSA), citric acid, trifluoroacetic acid (TFA), sulfuric acid, hydrochloric acid or a mixture thereof, preferably PTSA (notably in catalytic amount such as from 0.02 to 0.2 mol, notably at about 0.1 mol per mole of compound of formula (III)).

The dehydration reaction can be carried out in a solvent such as tetrahydrofuran (THF), 2-methyltetrahydrofuran (MeTHF), toluene or a mixture thereof, preferably toluene.

Preparation of Alcohol of Formula (III):

The alcohol of formula (III) can be prepared by methylation of a ketone of the following formula (IV):

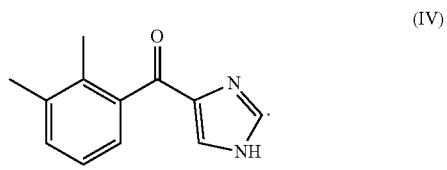

The methylation reaction can be performed in the presence of MeLi or MeMgHal$_1$ with Hal$_1$ representing a halogen atom such as Cl, Br or I, preferably MeMgCl.

The methylation step can be carried out in a solvent such as tetrahydrofuran (THF), dioxane, dimethoxyethane (DME), dichloromethane (DCM) or a mixture thereof. Preferably, it is performed in THF, notably at reflux.

Preparation of Ketone of Formula (IV):

The ketone of formula (IV) can be prepared by coupling a halide of the following formula (V):

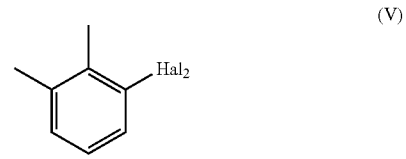

in which Hal$_2$ represents a halogen atom such as Br, with a cyanoimidazole of the following formula (VI):

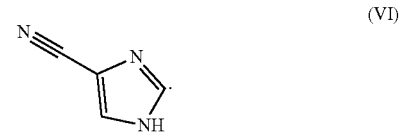

More particularly, the coupling reaction involves the following steps:

converting the halide of formula (V) into a Grignard reagent of the following formula (D), notably in the presence of magnesium:

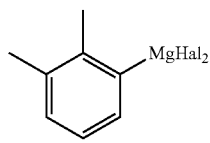
(D)

in which Hal$_2$ represents a halogen atom such as Br;

reacting the Grignard reagent of formula (D) with the cyanoimidazole of formula (VI) in order to form an imine of the following formula (E), notably after deprotonation (of the NH function) of the cyanoimidazole of formula (VI), for example with AlkMgHal$_3$ in which Alk represents a (C$_1$-C$_6$)alkyl such as iPr and Hal$_3$ represents a halogen atom such as Cl:

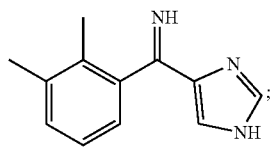
(E)

hydrolysing the imine of formula (E) in order to form the ketone of formula (IV), notably by treatment with an acid such as sulfuric acid, notably in an aqueous solution.

This coupling reaction can be performed in a solvent such as THF.

The conversion of the halide of formula (V) into a Grignard reagent is notably performed at a temperature of from 50 to 70° C., notably under reflux of THF.

The deprotonation of the cyanoimidazole of formula (VI) to form a magnesium halide derivative and the reaction of the Grignard reagent with the cyanoimidazole of formula (VI), in particular after the deprotonation step (i.e. reaction of the Grignard reagent with a magnesium halide derivative), are advantageously performed at a temperature equal to or below 0° C., notably from −10° C. to 0° C.

The reaction of the Grignard reagent of formula (D) with the cyanoimidazole of formula (VI), in particular after the deprotonation step (i.e. reaction of the Grignard reagent with a magnesium halide derivative), involves the reaction of the Grignard moiety on the nitrile function in order to form an imine. If the NH function of the imidazole unit is deprotonated to form the corresponding magnesium halide derivative beforehand, the Grignard moiety will not react with this function so as to avoid secondary reactions. The formation of the final imine of formula (E) involves notably a treatment in order to cleave the magnesium halide group, notably in the presence of water, at the end of the reaction between the Grignard reagent of formula (D) with the cyanoimidazole of formula (VI). Such a treatment can be simultaneous with the hydrolysing step.

The hydrolysing step is more particularly performed by adding an acid (e.g. sulfuric acid), and more particularly an aqueous solution of this acid, to the reaction medium.

An additional treatment with a base such as ammonium hydroxide can be performed in order to precipitate the ketone of formula (IV), which allows its separation from the reaction medium by filtration.

According to a particular embodiment, the coupling reaction is carried out as follows:

2,3-dimethylbromobenzene is reacted with magnesium in THF in the presence of 1,2-dibromoethane to form the corresponding Grignard reagent;

4-cyano-imidazole is converted to its magnesium chloride derivative with isopropylmagnesium chloride in THF (involving the deprotonation of its NH function and formation of a magnesium chloride derivative);

the magnesium chloride derivative of 4-cyano-imidazole is reacted with the solution of Grignard reagent to form an imine intermediate;

the imine intermediate is treated with sulfuric acid (in particular an aqueous solution of sulfuric acid) to form the desired ketone;

the ketone is precipitated by addition of ammonium hydroxide and then recovered by filtration.

The coupling between the halide of formula (V) and the cyanoimidazole of formula (VI) is performed advantageously with a molar ratio of cyanoimidazole of formula (VI)/halide of formula (V) of from 1:1 to 1:1.5, notably from 1:1.1 to 1:1.4, such as from 1:1.2 to 1:1.3.

The deprotonation step is performed notably with a molar ratio of cyanoimidazole of formula (VI)/AlkMgHal$_3$ of from 1:1 to 1:1.5, notably from 1:1.1 to 1:1.4, such as from 1:1.2 to 1:1.3.

Step b):

The salification and/or solvatation step can be carried out by methods well known to the one skilled in the art, in particular by reaction of the compound of formula (I) obtained in step (a) with a pharmaceutically acceptable acid (organic or inorganic acid), base (organic or inorganic base) or solvent, as defined previously. The solvent can be notably the solvent used in the last step of the preparation of the compound according to the invention.

According to a preferred embodiment, step b) is performed by adding a pharmaceutically acceptable acid and more particularly HCl so as to form dexmedetomidine hydrochloride. Such a salification step, in particular with HCl, can be performed in a solvent such as ethyl acetate, ethanol or a mixture thereof, preferably ethanol.

Step b) can be followed by a recrystallisation step of the pharmaceutically acceptable salt and/or solvate of dexmedetomidine, which allows recovering the final product by filtration. In particular, when dexmedetomidine hydrochloride is formed, it can be recrystallized in a solvent such as acetone.

The present invention is illustrated by the following non-limitative examples.

ABBREVIATIONS

DCM: Dichloromethane
DMSO: Dimethylsulfoxide
GC: Gas chromatography
HPLC: High Performance Liquid Chromatography
IPA: Isopropyl alcohol
IPC: In-Process Control
MeTHF: 2-Methyltetrahydrofuran
NMR: Nuclear Magnetic Resonance
T: Temperature
THF: Tetrahydrofuran

EXAMPLES

Dexmedetomidine hydrochloride has been synthesized according to the following scheme:

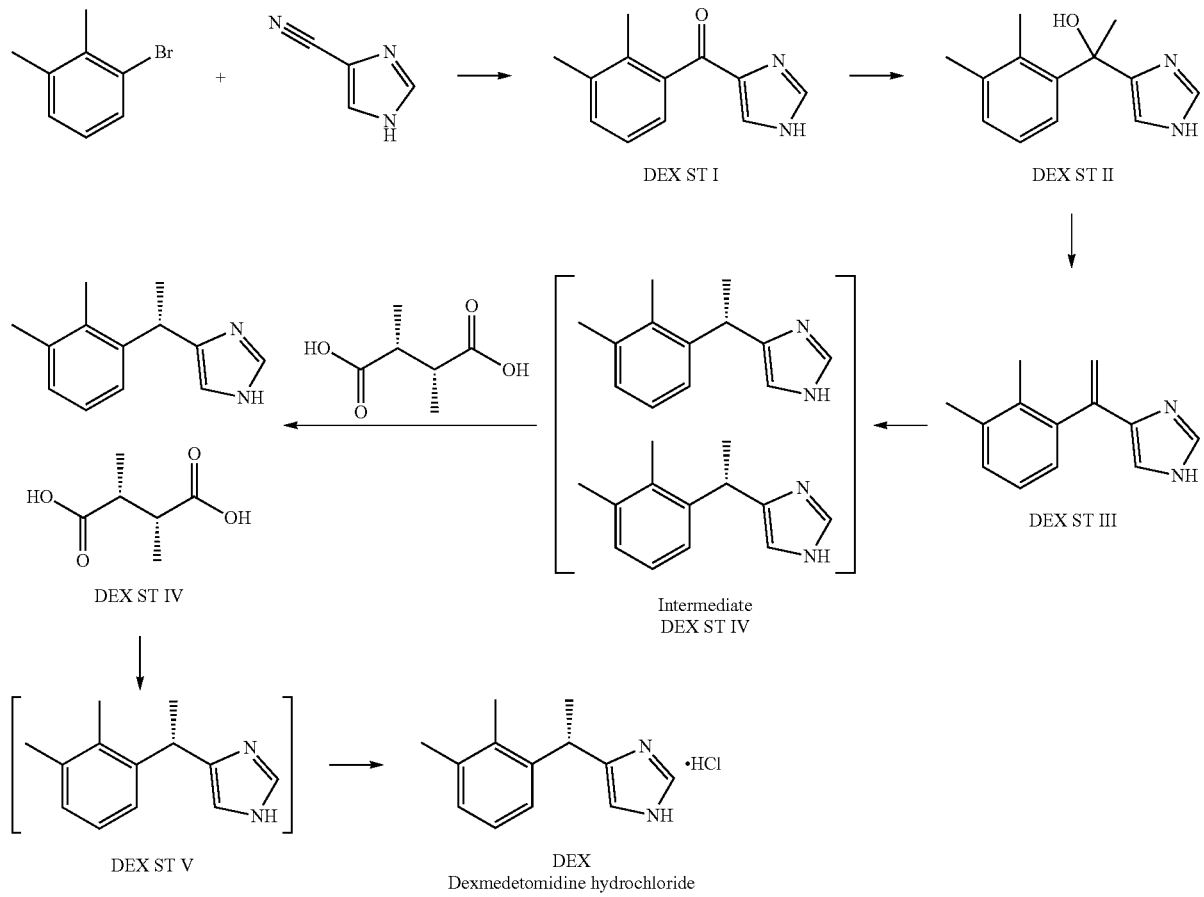

DEX ST I

THF (2.7 L, 7 vol) and magnesium (181.6 g, 1.8 eq) are charged under vigorous stirring in a suitable sized glass reactor. The mixture is heated to 40-45° C., then 1,2-dibromoethane (23.3 g, 0.03 eq) is added followed by 5% of a solution of 2,3-dimethylbromobenzene (998.2 g, 1.3 eq) in THF (6.5 L, 17 vol). Once the reaction is successfully initiated (exothermicity and grey/greenish coloration of the reacting mixture), the rest of the solution of 2,3-dimethylbromobenzene in THF is added. The mixture is stirred for at least 1 h at reflux (60-65° C.) until conversion is ≥97% (IPC by GC), then cooled down slowly to about 30° C. and stored under nitrogen (solution A). THF (20 L, 50 vol) and 4-cyanoimidazole (386 g, 1 eq) are charged under stirring in another suitable sized glass-lined reactor, and the mixture is cooled down to T≤−5° C., after which isopropylmagnesium chloride solution (2.90 kg, 2M in THF, 1.3 eq) is added maintaining T≤0° C. The filtered solution A is introduced carefully into the reacting mixture, maintaining T≤0° C. The mixture is stirred at T≤0° C. for at least 2 h until conversion is ≥90% (IPC by HPLC). Cold aqueous sulfuric acid solution (1.66 kg, 4 eq of $H_2SO_4$; in 7 L of deionized water, 20 vol) is added while maintaining T≤30° C. The mixture is stirred for at least 3 h until conversion is ≥99.0% (IPC by HPLC). Heptane (7 L, 18 vol) and deionized water (5 L, 13 vol) are added. After about 10 min of stirring, the layers are decanted. The aqueous layer is washed with heptane (7 L, 18 vol) for 10 min then separated. The isolated aqueous layer is cooled down to 0-5° C. under stirring, and 20.5% ammonium hydroxide solution (4.5 kg) is added until 9.8≤pH≤10.2 while maintaining T≤10° C. The resulting suspension is stirred at 0-5° C. for a minimum of 30 min, filtered through a glass filter, and the cake is washed with deionized water (4×4.3 L, 4×11 vol) and heptane (2×2.7 L, 2×7 vol). The product is dried under vacuum at 50° C. for at least 16 h. End of drying is checked by IPC (KF≤0.5% and assay [$HClO_4$]≥95%). Yield=80%.

DEX ST II

THF (5.8 L, 10 vol) and DEX ST I (580 g, 1 eq) are charged in a suitable sized glass reactor, and the mixture is stirred until obtaining complete dissolution. Water content of the solution is checked by IPC (KF<0.1%). The solution is heated to about 40° C. and methylmagnesium chloride solution (3M in THF, 3.08 kg, 3 eq) is added while maintaining temperature at 40-55° C. The mixture is stirred at reflux (60-65° C.) for at least 2 h until conversion is ≤99.5% (IPC by HPLC), then cooled down slowly to 0-5° C. A saturated solution of ammonium chloride (863 g, 5.6 eq) in deionized water (2.32 L, 4 vol) is added to the mixture while maintaining T≤10° C., then deionized water (4.64 L, 8 vol) and concentrated HCl (650 mL) are successively added until pH=7 while maintaining T≤30° C. After about 10 min of stirring, the aqueous layer is decanted and extracted with EtOAc (2×1.16 L, 2×2 vol). The organic layers are gathered and washed with brine (835 g of NaCl, 5 eq; in 2.32 L of deionized water, 4 vol). The organic layer is separated and the solvent is partially removed under reduced pressure (T≈60-70° C.) until $V_{dist}$≈15 vol, then heptane (4.6 L, 8 vol) is added and distillation is resumed under reduced pressure (T≈60-70° C.) until $V_{dist}$≈15 vol. The mixture is checked for residual THF and EtOAc (% THF<50% w/w and % EtOAc<30% w/w by NMR), then is cooled down to 15-25° C. and stirred for at least 1 h. The resulting suspension is filtered through a glass filter and the cake is washed with heptane (2×1.16 L, 2×2 vol). The solid is dried under vacuum at 40° C. for at least 16 h. End of drying is checked by IPC (loss on drying≤0.5%). Yield=100%.

In an alternative manner, DEX ST II can be prepared as follows.

DEX ST I (1.00 g, 1 eq) is suspended in a mixture of 1,2-dimethoxyethane (10 mL) and DCM (0.5 mL). After cooling at 4° C. in an ice/water bath, methylmagnesium chloride solution in THF (5.09 g; 22% w/w, 3 eq) is added over 21 min while keeping the internal temperature below 8° C. The ice bath is then removed. Conversion reached 100% by NMR (DMSO-$d_6$) after 1 h. The solution is stirred for a total of 18 h, during which a suspension formed. The mixture is cooled at 4° C. in an ice/water bath, and a solution of ammonium chloride (0.60 g, 60% w/w) in deionized water (4 mL) is added over 3 min. Concentrated hydrochloric acid is then added until pH=9 (0.80 g, 80% w/w). After 10 min of stirring, the aqueous layer is decanted, and concentrated hydrochloric acid is added again until pH=7-8. The resulting aqueous solution is extracted with ethyl acetate (2×3 mL). The combined organic layers are washed with brine (5 mL) and concentrated to dryness under vacuum. The resulting solid is slurried in heptane (5 mL) for 15 min, filtered on sintered glass, washed with heptane (2×2 mL) and dried under vacuum at 45° C. for 30 min. Yield=81.5%.

In another alternative manner, DEX ST II can be prepared as follows.

DEX ST I (54.48 g, 1 eq) is suspended in 1,2-dimethoxyethane (545 mL). After cooling at 2° C. in an ice/water bath, methylmagnesium chloride solution in THF (277.5 g; 22% w/w, 3 eq) is added over 33 min while keeping the internal temperature below 10° C. The ice bath is then removed. Conversion reached 100% by NMR (DMSO-$d_6$) after 1.5 h. The solution is stirred for a total of 2 h 15. The mixture is cooled at 13° C., and a solution of ammonium chloride (32.69 g, 60% w/w) in deionized water (218 mL) is added over 8 min. Concentrated hydrochloric acid is then added until pH=7 (47 mL). The aqueous layer is decanted, diluted with deionized water (250 mL) and extracted with ethyl acetate (2×200 mL). The combined organic layers are washed with brine (150 mL) and the solvents were distilled under atmospheric pressure until 745 mL of distillate is collected; a suspension appeared. The distillation is continued with portionwise addition of heptane (5×100 mL) until a total of 1085 mL of distillate is collected. The suspension is cooled to 27° C. in a water bath then at 1.8° C. in an ice/water bath, filtered on sintered glass, washed with cold heptane and dried under vacuum at 50° C. for 4 h. Yield=96%.

DEX ST III

Toluene (3.0 L, 5 vol), DEX ST II (600 g, 1 eq) and para-toluenesulfonic acid monohydrate (52.7 g, 0.1 eq) are charged under stirring in a suitable sized glass reactor, and the resulting suspension is heated at reflux (≈110° C.) for at least 2 h, eliminating water in Dean-Stark conditions, until conversion is ≥99% (IPC by HPLC). The mixture is then cooled down to 45-50° C., and a saturated solution of sodium bicarbonate (115.3 g, 0.5 eq) in deionized water (1.2 L, 2 vol) is carefully added at ≈80 mL/min. Crystallization is checked (≈38° C.). The suspension is stirred at 20-25° C. for 2 h prior to filtration through a glass filter. The cake is washed with water (1.2 L, 2 vol) and heptane (1.2 L, 2 vol), and the solid is dried under vacuum at 45° C. for at least 16 h until KF<1%. Yield=100%.

In an alternative manner, DEX ST III can be prepared as follows.

A mixture of DEX ST II (20 g, 1 eq), para-toluenesulfonic acid monohydrate (1.8 g, 0.1 eq) and citric acid monohydrate (19.4 g, 1 eq) in 2-methyltetrahydrofuran (MeTHF, 300 mL) is heated at reflux (75-78° C.) for a total of 14 h. Conversion reached 98.2% by HPLC. After cooling down to 20-25° C., deionized water (50 mL) is added followed by saturated aqueous sodium bicarbonate (250 mL) until pH=7. The aqueous layer is decanted and extracted with MeTHF (50 mL). The combined organic layers are concentrated to dryness at 40° C. under vacuum. Yield=90.5%.

DEX ST IV

Preparation of Intermediate DEX ST IV which is not Isolated

Methanol (24 L, 45 vol) is charged in a suitable sized glass-lined hydrogenation reactor under nitrogen and degassed with nitrogen. DEX ST III (520 g, 1 eq) is added, and the reactor is purged 3 times with nitrogen (3 bars).

In another suitable sized glass-lined reactor, bis(norbornadiene) rhodium tetrafluoroborate (9.83 g, 0.01 eq), (S)-(+)-1-[(R)-2-diphenylphosphinoferrocenyl]ethyldi-tert-butylphosphine (14.24 g, 0.01 eq) and methanol (520 mL, 1 vol, previously degassed with nitrogen) are introduced. The mixture is stirred at 20-25° C. until complete dissolution, then the resulting catalyst solution is quickly transferred under nitrogen into the first reactor. The hydrogenation reactor is purged 3 times with nitrogen (3 bars) and then 3 times with hydrogen (10 bars). The reaction mixture is kept at 40-45° C. under 10 bars of hydrogen for at least 5 h until conversion is 99.5% (IPC by HPLC). After cooling down to 25° C., the reactor is purged 3 times with nitrogen (3 bars), and the reaction mixture is concentrated under vacuum at T≤40° C. until distillation stops. Acetone (5.2 L, 10 vol) is introduced and the mixture is concentrated again under vacuum at T≈40° C. At this point, the enantiomeric purity is checked by reporting the % of dexmedetomidine and levomedetomidine (IPC by chiral HPLC). % e.e.=79.3%.

Preparation of DEX ST IV from Intermediate DEX ST IV

Acetone (5.2 L, 10 vol) is added and the suspension is stirred at room temperature. After transfer of the suspension into a suitable sized glass reactor, water (520 mL, 1 vol) is added and the mixture is heated to 45-50° C. until an orange solution is obtained. L-(+)-tartaric acid (390.5 g, 1 eq) is introduced under vigorous stirring, and the mixture is stirred at 50-55° C. for at least 30 min. After cooling down slowly to 20-30° C., the resulting suspension is filtered through a glass filter. The cake is washed with acetone (1.04 L, 2 vol) and dried under vacuum at 50° C. for at least 12 h. End of drying is checked by IPC (loss on drying≤0.5%). Yield=85%. % e.e.=95.7%.

In an alternative manner, DEX ST IV can be prepared as follows from Intermediate DEX ST IV.

Deionized water (35 mL) is added to a solution of Intermediate DEX ST IV (140.4 g, 1 eq) in methanol (422 mL). L-(+)-tartaric acid (105.2 g, 1 eq) is then added portionwise. Acetone (702 mL) is added to the thick suspension, and the resulting mixture is heated at 50-60° C. for 1.5 h. After cooling down to 20° C. in a cold-water bath, the solid is filtered on sintered glass, washed with acetone (281 mL) and dried at 50° C. under vacuum for 1 h. Yield 83.7%. HPLC (% area)=98.65%. % e.e.=94.8%.

The DEX ST IV L-tartaric salt formed can also be treated according to one of the following methods (1) to (4).

(1) DEX ST IV L-tartaric salt (1 g, % e.e. 88.94%) is then suspended in a mixture of deionized water (1 mL) and acetone (1 mL), and the suspension was heated at 60° C. for 1 h before slowly cooling down to 20-25° C. The solid was filtered and washed with 2 mL of acetone. Yield 89%. % e.e.=94.16%.

(2) DEX ST IV L-tartaric salt (1 g, % e.e. 88.94%) was suspended in a mixture of deionized water (1 mL) and acetonitrile (1 mL), and the suspension was heated at 60° C. for 1 h before slowly cooling down to 20-25° C. The solid was filtered and washed with 2 mL of acetonitrile. Yield 87%. % e.e.=93.02%.

(3) DEX ST IV L-tartaric salt (1 g, % e.e. 88.94%) was suspended in a mixture of deionized water (1 mL) and ethanol (1 mL), and the suspension was heated at 60° C. for 1 h. The resulting solution was then slowly cooled down to 20-25° C. The solid was filtered and washed with 2 mL of ethanol. Yield 85%. % e.e.=98.68%.

(4) DEX ST IV L-tartaric salt (1 g, % e.e. 88.94%) was suspended in a mixture of deionized water (1 mL) and isopropanol (1 mL), and the suspension was heated at 60° C. for 1 h. The resulting solution was then slowly cooled down to 20-25° C. The solid was filtered and washed with 2 mL of isopropanol. Yield 80%. % e.e.=96.74%.

In an alternative manner, a DEX ST IV' dibenzoyl-L-tartaric salt is formed instead of the DEX ST IV L-tartaric salt by using dibenzoyl-L-tartaric acid instead of L-(+)-tartaric acid and it can be prepared as follows from DEX ST III.

(S)-(+)-1-[(R)-2-(diphenylphosphino)ferrocenyl]-ethyl di-tert-butyl phosphine (137 mg, 0.01 eq) and bis(norbornadiene)rhodium tetrafluoroborate (94 mg, 0.01 eq) are dissolved in degassed methanol (1 mL) in a glove box under $N_2$. The resulting red solution is added to a mixture of DEX ST III (5.0 g, 1 eq) in degassed methanol (45 mL) in a hydrogenation bomb. The mixture is heated at 50° C. under 10 bar of hydrogen for 22 h. IPC by HPLC (% area) shows 99.9% conversion.

After flushing with $N_2$ and cooling to 20-25° C., the orange solution is transferred to a round-bottomed flask and dibenzoyl-L-tartaric acid (9.03 g, 1 eq) is added under stirring. After 3 h 45, the mixture is concentrated to dryness under vacuum, and the residue is stirred in methanol (1.5 mL) and acetone (22 mL) to give a suspension. After stirring overnight, the solid is filtered on sintered glass, washed with acetone (4×10 mL) and dried under vacuum at 40° C. Yield=47%. % e.e.=94.00%.

DEX STV

Ethanol (denatured with 3% IPA, 7.55 L, 10 vol), DEX ST IV (755 g, 1 eq) and deionized water (755 mL, 1 vol) are charged into a suitable sized glass reactor. The resulting suspension is heated to 65-70° C. until complete dissolution, then left to cool to 30-35° C. in about 2 h. At 30-35° C., crystallization is initiated by seeding with a sample of pure Dexmedetomidine. The mixture is then cooled down to 20-25° C. over 30-60 min, and the suspension is filtered through a glass filter. The cake is washed with ethanol (denatured with 3% IPA, 1.5 L, 2 vol). A sample of the wet cake is dried to determine the mass in wet product ($M_{WP}$). An IPC is performed on the wet product to check the enantiomeric purity (Levomedetomidine≤0.1% and Dexmedetomidine≥99.9% by chiral HPLC) and water content. If not conform, the previous purification is repeated based on the calculated $M_{WP}$ and water content. If conform, ethanol (denatured with 3% IPA, 5.78 L, 8 vol; adjusted taking into account the ethanol content of the wet solid) and deionized water (598 mL, 0.8 vol; adjusted taking into account the water content of the wet solid). The resulting suspension is heated to 65-70° C. until complete dissolution, then left to cool to 20-25° C. for at least 1 h, and stirred at this temperature for a minimum of 1 h. The suspension is filtered through a glass filter and the cake is washed with ethanol (denatured with 3% IPA, 1.19 L, 1.6 vol).

The wet solid is reintroduced into the glass-lined reactor along with deionized water (5.78 L, 7.6 vol). The pH is adjusted to 10 by addition of concentrated sodium hydroxide solution (386.5 g). The resulting suspension is stirred at 15-25° C. for 30 min, then filtered through a glass filter. The cake is washed with deionized water (2×330 mL, 2×0.4 vol), and the solid is dried under vacuum at 60° C. for at least 12 h until KF<1%. Yield=75% (2 purification steps). If 3 purification steps are used, yield=65%. % e.e.=100%.

DEX

Ethanol (denatured with 3% IPA, 1.325 L, 5 vol) and DEX ST V (265 g, 1 eq) are charged into a suitable sized glass reactor. The suspension is heated at 35-40° C. until complete dissolution. The resulting yellow solution is filtered through a GFA filter; the reactor and the filter are rinsed with ethanol (denatured with 3% IPA, 2×27 mL, 2×0.1 vol). The filtrate is transferred into another suitable sized glass reactor, and previously filtered concentrated hydrochloric acid (150 mL, 1.3 eq) is added. The resulting nearly colorless solution is concentrated under vacuum at T<50° C. until minimum volume. The mixture is cooled to T<40° C. and the pressure is set to atmospheric pressure, then filtered acetone (265 mL, 1 vol) is added. The volume $V_R$ of the reaction mixture is noted, and filtered acetone (1.06 L, 4 vol) is added. The mixture is concentrated at T<50° C. under reduced pressure until volume $V_R$. After cooling down to T<40° C., filtered acetone (1.325 L, 5 vol) is added at atmospheric pressure, and the mixture is concentrated at T<50° C. under reduced pressure until volume $V_R$. This step is repeated one more time. Filtered acetone (1.06 L, 4 vol) is added, and the mixture is cooled down to 20-25° C. and stirred at this temperature for at least 20 min. The suspension is filtered through a glass filter, and the cake is washed with filtered acetone (530 mL, 2 vol) previously used to rinse the reactor. The product is dried under vacuum at 45° C. during at least 12 h. End of drying is checked by IPC (loss on drying<0.75%). Yield=90%. % e.e.=100%.

The invention claimed is:
1. A method for preparing dexmedetomidine having the following formula (I):

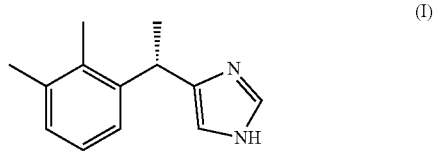

or a pharmaceutically acceptable salt and/or solvate thereof,
comprising the following successive steps:
a) asymmetric hydrogenation of a methylene derivative of the following formula (II):

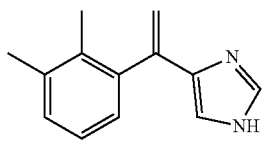

(II)

in order to obtain dexmedetomidine,
the asymmetric hydrogenation of the methylene derivative of formula (II) being performed in the presence of dihydrogen and a chiral catalyst of the following formula (A):

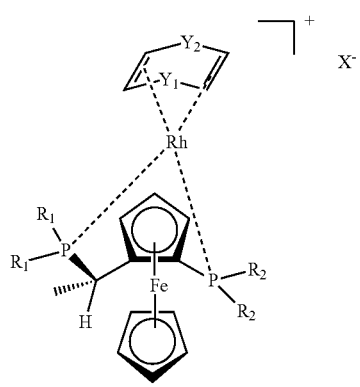

(A)

in which:
X⁻ is a counter-anion bearing one negative charge;
$Y_1$ and $Y_2$ form together a chain CH—CH$_2$—CH or each $Y_1$ and $Y_2$ represent a group CH$_2$CH$_2$; and
$R_1$ and $R_2$ independently of each other represent a $(C_1-C_6)$alkyl, a $(C_3-C_{10})$cycloalkyl, a heteroaryl or an aryl optionally substituted by one or several groups selected from $(C_1-C_6)$alkyl, $(C_1-C_6)$haloalkyl, $(C_1-C_6)$alkoxy, $(C_1-C_6)$alkylamino and di$((C_1-C_6)$alkyl)amino, and b) optionally salifying and/or solvating dexmedetomidine in order to obtain a pharmaceutically acceptable salt and/or solvate of dexmedetomidine,
wherein the methylene derivative of formula (II) is prepared from a halide of the following formula (V):

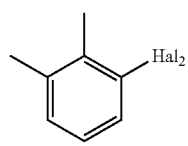

(V)

in which Hal$_2$ represents a halogen atom,
and a cyanoimidazole of the following formula (VI):

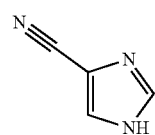

(VI)

according to the following steps:
i) coupling the halide of formula (V) with the cyanoimidazole of formula (VI) in order to obtain a ketone of the following formula (IV):

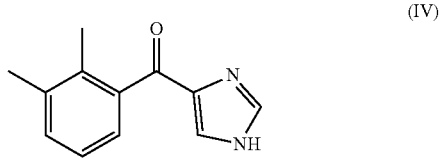

(IV)

according to the following steps:
converting the halide of formula (V) into a Grignard reagent;
deprotonating the cyanoimidazole of formula (VI) with AlkMgHal$_3$ in which Alk represents a $(C_1-C_6)$alkyl, and Hal$_3$ represents a halogen atom to form a magnesium halide derivative,
reacting the Grignard reagent with the magnesium halide derivative and then hydrolysing the reaction product thus obtained in order to form the ketone of formula (IV);
ii) methylating the ketone of formula (IV) in order to obtain an alcohol of the following formula (III):

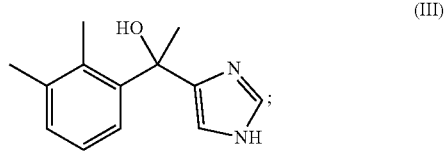 [SMILES: Cc1cccc(C(C)(O)c2c[nH]cn2)c1C]

(III)

and iii) dehydrating the alcohol of formula (III) in, order to obtain the methylene derivative of formula (II).

2. The method according to claim 1, wherein dexmedetomidine or a pharmaceutically acceptable salt and/or solvate thereof is dexmedetomidine hydrochloride so that step b) is performed in the presence of HCl.

3. The method according to claim 1, wherein the chiral catalyst of formula (A) is prepared from:
a non-chiral rhodium-based catalyst of following formula (B):

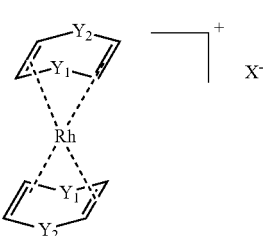

(B)

in which $Y_1$, $Y_2$ and X are as defined in claim 1, and a chiral ligand of the following formula (C):

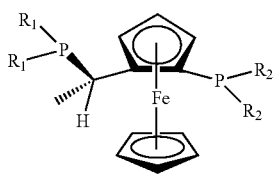

in which $R_1$ and $R_2$ are as defined in claim 1.

4. The method according to claim 3, wherein the non-chiral rhodium-based catalyst of formula (B) and the chiral ligand of formula (C) are used in step a) in the following amounts:
 amount of the non-chiral rhodium-based catalyst of formula (B): from 0.001 to 0.1 mol per mole of methylene derivative of formula (II) used in step a);
 amount of the chiral ligand of formula (C): from 0.001 to 0.1 mol per mole of methylene derivative of formula (II) used in step a).

5. The method according to claim 1, wherein the chiral catalyst of formula (A) is:

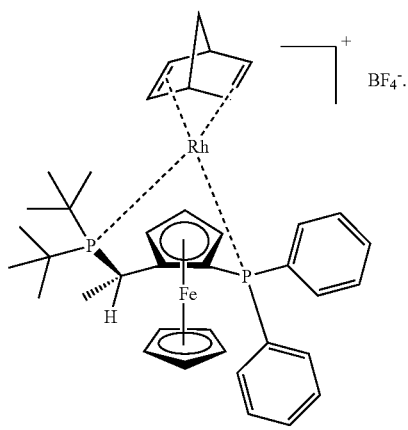

6. The method according to claim 1, wherein dexmedetomidine is obtained in step a) with an enantiomeric excess of at least 70%.

7. The method according to claim 1, wherein a step a') of enantiomeric enrichment is performed after step a).

8. The method according to claim 7, wherein the step a') of enantiomeric enrichment is performed before step b).

9. The method according to claim 7, wherein the enantiomeric enrichment is performed by:
 a'1) reacting the product of step a) with a chiral acid in order to form diastereoisomer salts, wherein one of these salts is a salt formed with dexmedetomidine;
 a'2) separating and recovering the salt formed with dexmedetomidine;
 a'3) optionally recrystallizing the salt formed with dexmedetomidine;
 a'4) converting the salt formed with dexmedetomidine into dexmedetomidine;
 a'5) optionally recrystallizing dexmedetomidine.

10. The method according to claim 7, wherein dexmedetomidine is obtained in step a') with an enantiomeric excess of from 95.0% to 100%.

11. The method according to claim 1, wherein dexmedetomidine or a pharmaceutically acceptable salt and/or solvate thereof is obtained at the end of the method with an enantiomeric excess of from 99.0% to 100%.

12. The method according to claim 1, wherein the dehydration of the alcohol of formula (III) is performed in the presence of an acid.

13. The method according to claim 12, wherein the acid used in the dehydration of the alcohol of formula (III) is para-toluenesulfonic acid (PTSA), citric acid, trifluoroacetic acid (TFA), sulfuric acid, hydrochloric acid or a mixture thereof.

14. The method according to claim 1, wherein the methylation of the ketone of formula (IV) is performed in the presence of MeLi or MeMgHal$_1$ with Hal$_1$ representing a halogen atom selected from Cl, Br and I.

15. The method according to claim 1, wherein the molar ratio of cyanoimidazole of formula (VI)/halide of formula (V) is of from 1:1 to 1:1.5.

16. The method according to claim 4, wherein the non-chiral rhodium-based catalyst of formula (B) and the chiral ligand of formula (C) are used in step a) in stochiometric amounts.

* * * * *